(12) United States Patent
Singh et al.

(10) Patent No.: US 6,307,058 B1
(45) Date of Patent: Oct. 23, 2001

(54) SELF-CROSSLINKING HYDROXY/ALKOXY ACYL IMIDAZOLIDINONE MONOMERS

(75) Inventors: Balwant Singh, Stamford; David Andrew Siesel, Trumbull; Laurence Wu-Kwang Chang, New Haven, all of CT (US)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 09/604,570

(22) Filed: Jun. 27, 2000

Related U.S. Application Data

(63) Continuation of application No. 08/881,781, filed on Jun. 24, 1997, now abandoned.
(60) Provisional application No. 60/020,999, filed on Jun. 24, 1996.

(51) Int. Cl.$^7$ .......................... C07D 233/40; C08F 226/06
(52) U.S. Cl. .................... 548/317.5; 524/555; 548/313.7
(58) Field of Search .......................... 548/317.5; 524/555

(56) References Cited

U.S. PATENT DOCUMENTS

| | | | |
|---|---|---|---|
| 2,727,016 | 12/1955 | Hankins et al. | 260/77.5 |
| 2,727,019 | 12/1955 | Melamed | 260/79.7 |
| 2,881,171 | 4/1959 | Hankins | 260/256.4 |
| 2,980,652 | 4/1961 | Melamed et al. | 260/77.5 |
| 3,194,792 | 7/1965 | Emmons et al. | 260/77.5 |
| 3,356,654 | 12/1967 | Sekmakas | 260/78.5 |
| 3,369,008 | 2/1968 | Hurwitz | 260/80.72 |
| 3,509,085 | 4/1970 | Sekmakas | 260/29.6 |
| 4,104,220 | 8/1978 | Sims | 260/29.6 R |
| 4,111,877 | 9/1978 | Dixon et al. | 260/29.6 R |
| 4,219,454 | 8/1980 | Iacoviello et al. | 260/29.6 T |
| 4,249,011 | * 2/1981 | Wendling | 548/312 |
| 4,262,072 | * 4/1981 | Wendling et al. | 430/14 |
| 4,284,536 | * 8/1981 | Bezwada | 548/317.5 X |
| 4,314,067 | 2/1982 | Herman et al. | 548/320 |
| 4,319,032 | 3/1982 | Sandri et al. | 548/320 |
| 4,426,503 | 1/1984 | Sandri et al. | 526/263 |
| 4,577,031 | 3/1986 | Iovine et al. | 548/319 |
| 4,596,850 | 6/1986 | Iovine et al. | 524/548 |
| 4,599,417 | 7/1986 | Sekmakas et al. | 544/316 |
| 4,617,364 | 10/1986 | Sekmakas et al. | 526/263 |
| 4,622,374 | 11/1986 | Iovine et al. | 526/263 |
| 4,730,045 | 3/1988 | Sekmakas et al. | 544/318 |
| 4,766,221 | 8/1988 | Floyd | 548/320 |
| 4,770,668 | 9/1988 | Skoultchi et al. | 8/181 |
| 4,777,265 | 10/1988 | Merger et al. | 548/320 |
| 4,783,539 | 11/1988 | Abboud et al. | 548/320 |
| 4,883,873 | 11/1989 | Abboud et al. | 544/316 |
| 4,985,453 | * 1/1991 | Ishii et al. | 514/386 |
| 5,210,199 | 5/1993 | Grosius et al. | 548/324.1 |
| 5,235,016 | 8/1993 | Vafa et al. | 526/304 |
| 5,498,723 | 3/1996 | Riondel et al. | 548/324.1 |
| 5,567,826 | 10/1996 | Knebel et al. | 548/324.1 |
| 5,610,313 | 3/1997 | Riondel et al. | 548/324.1 |

FOREIGN PATENT DOCUMENTS

| | | |
|---|---|---|
| 3706435 A | 9/1987 | (DE) . |
| 124713 A | 11/1984 | (EP) . |
| 240370 A | 10/1987 | (EP) . |
| 0629672 A2 | 12/1994 | (EP) . |
| 0629672 A3 | 12/1994 | (EP) . |
| WO91/12243 | 8/1991 | (WO) . |

OTHER PUBLICATIONS

S.M. Kambanis and G. Chip, "Polymer and Paint Properties Affecting Wet Adhesion," *Journal of Coatings Technology*, vol. 53, No. 682 (Nov. 1981), pp 57–64.

* cited by examiner

*Primary Examiner*—Floyd D. Higel
(74) *Attorney, Agent, or Firm*—Valerie T. Didamo; Claire M. Schultz; James A. Jubinsky

(57) ABSTRACT

Acyl imidazolidinones and compositions containing the same are disclosed, which are particularly suitable for use as self-crosslinkers and can also be used as wet adhesion properties, especially in latex-based polymer systems. Processes for preparing such compounds, compositions containing the same, as well as additional uses thereof are also disclosed.

3 Claims, No Drawings

SELF-CROSSLINKING HYDROXY/ALKOXY ACYL IMIDAZOLIDINONE MONOMERS

The present application is a continuation of parent application Ser. No. 08/881,781 filed Jun. 24, 1997, now abandoned, which claims the benefit of U.S. Provisional Application No. 60/020,999 filed Jun. 24, 1996, which is incorporated by reference herein as if fully set forth.

BACKGROUND OF THE INVENTION

1. Field of the Invention

This invention relates to novel polymerizable acyl imidazolidinones, their preparation and their utility in preparing self-crosslinking polymers and latices thereof. The polymerizable monomers of the present invention are also useful in paper and textile applications and in improving wet adhesion properties of latex paints.

2. Description of Related Art

It is well-known in the art to employ self-crosslinking polymers, either in emulsion or solution form, as coatings, binders or adhesives for a variety of substrates. Self-crosslinking polymers are distinguished from crosslinkable polymers in that the latter contain functionality such as a carboxyl group which can only be crosslinked by the addition of an external crosslinker to the polymer emulsion or solution. A typical crosslinkable system is a poly(carboxyl functional) polymer crosslinked with a polyepoxy crosslinker.

In contrast, self-crosslinking polymers contain reactive functionalities which allow these polymers to self-crosslink without the need for an external crosslinking agent. A typical crosslinking polymer containing N-methylolated amide functionalities, incorporated via N-methylolacrylamide, undergoes thermosetting crosslinking by splitting out a mole of formaldehyde. The advantages of the self-crosslinking polymer systems include their simplicity, economy, and particularly their efficiency. Such systems have been used in a variety of applications, including use as textile adhesives, nonwoven binders, pigment binders, fabric finishing agents, binders for paper and wood finishing applications.

Interior and exterior latex-based paints exhibit poor wet adhesion compared to solvent-based paints. The term wet adhesion is used in the paint industry to describe the ability of a paint to retain its adhesive bond to a substrate under wet or high humidity conditions. While oil-based systems are known to retain their adhesive properties under wet or humid conditions, the tendency of many water based coatings (i.e., latices) to lose their adhesive properties when wet has limited the usefulness of such coatings. The wet adhesion deficiency of latex paints also makes surfaces painted with such paints less scrub resistant than those surfaces painted with organic solvent based paints.

Since the use of water-based emulsion polymer systems as protective and decorative coatings for many types of surfaces has become widespread, such systems being used by individuals in homes and industrially, there is a great need for improved wet adhesion of aqueous emulsion polymer systems. In recent years, the art has recognized the problem of loss of adhesive properties in latex paints and a variety of additives to latex systems to improve wet adhesion have been proposed. Incorporation of amine, amide, acetoacetate, urea and ureido functionalities into latex polymers has been reported to improve the wet adhesion properties of latex paints. For example, an imidazolidinone compound (cyclic ureido) has been described in EP-A-0629672 as imparting wet adhesion properties to various latex systems, which reference is incorporated by reference herein for all purposes as if fully set forth.

U.S. Pat. Nos. 4,577,031, 4,596,850 and 4,622,374, and EP-A-0629672, specifically disclose polymerizable imidazolidinones and their use as self-crosslinking monomers which also improve the wet adhesion properties of latex paints. However, the self-crosslinking and wet adhesion promoter monomers of the aforementioned prior art have the disadvantage that they are expensive and their inclusion into latex polymers results in substantial increase in the final cost of latex-based paints.

It has now been found that self-crosslinking and wet-adhesion properties can be imparted to latex-based polymers and paints produced from such polymers by incorporating into the monomer system, from which the polymers are produced, one or more of the present invention's new class of acyl imidazolidinones. A unique advantage of the present invention's new class of compounds is that they can be made from inexpensive and readily obtainable raw materials, including urea, maleic anhydride and hydroxy and amino functional coreactants. Other suitable anhydrides from which the invention's new class of compounds can be made include citraconic anhydride and itaconic anhydride.

It has also been discovered that the novel higher alkyl esters and amides of the acyl imidazolidinones also provide sizing properties to paper and textiles. They can, therefore, be used as alternatives to sizing agents such as ACCOSIZE® 17 (Cytec Industries) and other paper treating agents, as, for example, those compounds disclosed in U.S. Pat. No. 2,727,016, which is herein incorporated by reference for all purposes as if fully set forth.

SUMMARY OF THE INVENTION

The present invention is directed to novel polymerizable acyl imidazolidinone monomers represented by the following general Formula (I)

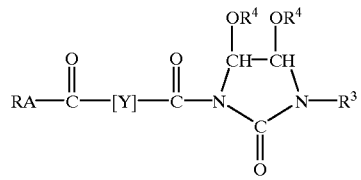

wherein A is —NH— or —O—;
wherein Y is

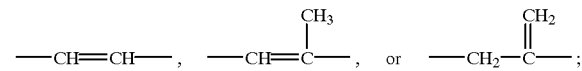

wherein R is H, an alkyl group having from 1 to 24 carbon atoms,

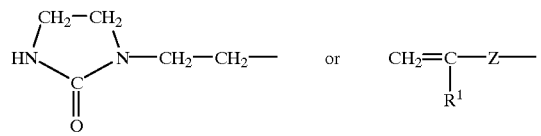

wherein Z is —CH$_2$—,

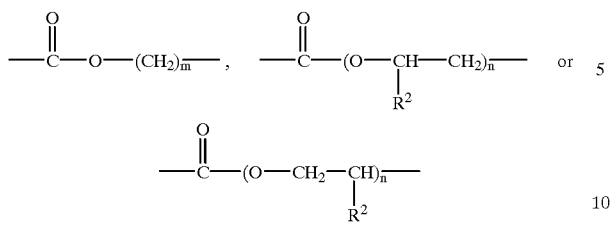

with the proviso that when A is —NH—, Z is —CH$_2$—;
wherein each R$^1$ or R$^2$ is, individually, hydrogen or CH$_3$, m is ≧2 and n is an integer of from 1–5, inclusive; and wherein R$^3$ is hydrogen, an alkyl group having from 1 to 4 carbon atoms, a hydroxymethyl or an alkoxymethyl having from 2 to 6 carbon atoms, and each R$^4$ is, individually, hydrogen or an alkyl group having from 1 to 6 carbon atoms.

Both the cis- and trans-stereoisomers of the above compounds, where appropriate (e.g., maleic and fumaric), are included within the above definition. It is also within the scope of the invention to use mixtures of the novel compounds of Formula (I) in aqueous emulsion polymer systems.

It is an object of this invention to provide economically obtainable novel acyl imidazolidinones for use as self-crosslinking monomers and a process for producing such monomers.

It is a further object of this invention to provide a method of crosslinking a polymer by adding to that polymer the novel monomers of the present invention.

The Invention is also directed to the use of the novel acyl imidazolidinones to form self-crosslinking polymers either in emulsion or solution form, as coatings, binders or adhesives for a variety of substrates.

Accordingly, the invention includes compositions comprising the monomers of Formula (I) of the present invention, polymers made therefrom and compositions, including acrylic, vinyl and vinyl-acrylic latex paints comprising polymers, made from the monomers of this invention.

These and other features and advantages of the present invention will be more readily understood by those skilled in the relevant art from a reading of the following detailed description.

DETAILED DESCRIPTION OF THE PREFERRED EMBODIMENTS

As indicated above, the present invention relates most broadly to novel acyl imidazolidinones of the general Formula (I), shown above. They are dihydroxy/alkoxy derivatives of acyl imidazolidinones which are referred to herein as glycomaleuric acid, glycofumauric acid, glycocitraconuric acid, glycoitaconuric acid, glycomaleurates, glycofumaurates, glycocitraconurates, glycoitaconurates, glycomaleuramides, glycofumauramides, glycocitraconuramides and glycoitaconuramides. These novel compounds are distinguished from the imidazolidinones of the prior art by the fact that the imidazolidinone rings are attached to a carbonyl (C=O) rather than an alkylene group. These novel compounds are therefore termed acyl imidazolidinones rather than alkylene imidazolidones as described in the prior art. The presence of the additional carbonyl groups not only increases the polarity of the molecules but also alters their reactivity profiles.

Preparation of the Novel Acyl Imidazolidinones

The monomers of the present invention are prepared from such known compounds as N-carbamylmaleimide (NCMI), N-carbamylcitraconimide (NCCI) and N-carbamylitaconimide (NCII), which compositions have the Formulae shown below:

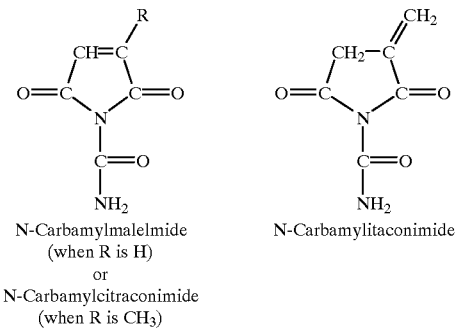

N-Carbamylmalelmide
(when R is H)
or
N-Carbamylcitraconimide
(when R is CH$_3$)

N-Carbamylitaconimide

In a first step, NCMI, NCCI or NCII are reacted with the hydroxy and amino functional coreactants to form the maleurate, citraconurate, itaconurate esters and the amides which are subsequently reacted with glyoxal to produce the corresponding glyoxylated derivatives. The glyoxylated derivatives are referred to as glycomaleurates, glycocitraconurates, glycoitaconurates, glycomaleuramides, etc. The corresponding trans isomers, glycofumaurates, glycofumauramides and the like are prepared via glyoxylation of the corresponding trans fumaurates, fumauramides, etc. as more specifically detailed below.

Hydroxy and amino functional coreactants include C$_1$–C$_{24}$ aliphatic/alicyclic/aralkyl alcohols and amines, unsaturated alcohols such as allyl alcohol, methallyl alcohol, hydroxyalkyl acrylates, hydroxyalkyl methacrylates, hydroxyethylethyleneurea, hydroxyethylpropyleneurea, aminoethylethyleneurea, aminoethylpropyleneurea, allylamine, methallylamine, diallylamine and dimethallylamine and the like.

The esters of hydroxyalkyl acrylates and methacrylates are referred to herein as acrylated glycomaleurates, glycofumaurates, glycocitraconurates and glycoitaconurates. The hydroxyethylethyleneurea and aminoethyleneurea derivatives are referred to herein as cyclic urea glycomaleurates, glycofumaurates, glycocitraconurates, glycoitaconurates, glycofumauramides, and glycomaleuramides, and the like. The allyl and methallyl derivatives are referred to herein as allyl glycomaleurates, alkyl glycofumaurates, allyl glycocitraconurates, allyl glycoitaconurates, allyl glycofumauramides, allyl glycoitaconuramides and the like. The alkyl derivatives are referred to as alkyl glycomaleurates, alkyl glycofumaurates, alkyl glycocitraconurates, alkyl glycoitaconurates, alkyl glycofumauramides, alkyl glycoitaconuramides and the like. The glyoxylated derivatives of maleuric acid, fumauric acid, maleuramides, fumauramides, citraconuric acid and itaconuric acid are referred to as glycomaleuric acid, glycofumauric acid, glycofumauramides, glycocitraconuric acid and glycoitaconuric acid.

The above-described glyoxylated monomers may be further etherified with alcohols to form alkoxy derivatives. All these materials may subsequently be reacted with formaldehyde and or formaldehyde/alcohols to produce methylolated and alkylmethylolated(alkoxymethyl) derivatives of these monomers.

A method of producing the maleurate, citraconurate and itaconurate monomers of the present invention is to react N-carbamylmaleimide (NCMI), N-carbamylcitraconimide (NCCI) or N-carbamylitaconimide (NCII) with the appropriate hydroxy or amino functional compounds. For example, the acrylated maleurates, citraconurates and itaconurates are prepared by reacting NCMI, NCCI or NCII with hydroxyalkyl acrylates and methacrylates in essentially stoichiometric quantities at a temperature range of from about 20° C. to 150° C. Preferably, the temperature ranges from about 25° C. to about 100° C. Examples of suitable hydroxyalkyl acrylates and methacrylates include 2-hydroxyethyl acrylate, 2-hydroxyethyl methacrylate, 2-hydroxypropyl acrylate, 2-hydroxypropyl methacrylate and ethoxylated and propoxylated acrylic and methacrylic acid, and the like.

In order to lower the viscosity of the reaction mixture, a non-hydroxylic solvent may be employed. Examples of suitable non-hydroxylic, non-reactive solvents include acetonitrile, acetone, methyl ethyl ketone, dioxane, tetrahydrofuran, ethylene glycol dimethyl ether, dimethylformamide, dimethylacetamide, dimethylsulfoxide, aromatic hydrocarbons such as toluene and xylene, and the like.

The reaction may optionally be carried out in the presence of other comonomers such as methyl methacrylate, methacrylic acid, styrene and mixtures thereof. These optional comonomers do not enter into the above-described reaction and their sole function is to allow the final product, that is the novel acrylated maleurate monomer, to exist in solution form.

A catalyst is not necessary for the reaction but if desired, a catalyst may be added to accelerate the reaction. Suitable catalysts include $ZnCl_2$, $Zn(OCOCH_3)_2$, $FeCl_3$ cobalt acetate, chelates of transition metal ions with $\alpha,\beta$-diketones and ketoesters, tin salts such as $SnCl_2$, $SnCl_4$, $SnO_2$ and tin based urethane catalysts such as dibutyltin dilaurate, tetrabutyldiacetoxy-stannoxane, dimethyltin dilaurate, stannous octoate and dibutyltin oxide. The preferred catalysts are the zinc and tin compounds. The amount of catalyst generally used is 0.1 to 5.0 mole percent based on NCMI, NCCI or NCII. Preferably, the range of catalyst used is from about 0.1 to 1.0 mole %.

To prevent polymerization of the reactants and/or the product, it is customary to use low levels of radical inhibitors. Examples of suitable inhibitors include the methyl ether of hydroquinone, di-tert-butyl catechol, di-tert-butyl phenol, phenothiazene, etc. The total inhibitor concentration is typically in the range from about 100 to 500 ppm. The preferred range of radical inhibitor is from about 200 to 250 ppm of methyl ether of hydroquinone.

The above-described reaction of NCMI, NCCI or NCII with hydroxyalkyl acrylates and methacrylates yields novel acrylated monomers. If it is desired to prepare the novel acrylated monomers so that they are not in solution form as a final product, the optional monomers described above are not added and the acrylated monomers are isolated by removal, under reduced pressure, of the non-hydroxylic (non-reactive) solvent (i.e., acetonitrile, acetone) used, if any, followed by aqueous washing of the novel acrylated maleurate product with water, followed by drying.

The cyclic urea derivatives of NCMI, NCCI or NCII are prepared by reacting these cyclic imides with hydroxyethylethyleneurea and aminoethylethyleneurea in essentially stoichiometric amounts. As in the case of the acrylic derivatives, the reaction is preferably carried out in the temperature range of 20° C. to 150° C., more preferably in the 25° C. to 100° C. The reaction with aminoethylethyleneurea is best carried out in the 20°–50° C. range to avoid by-product formation. The reaction is preferably carded out in the presence of one or more of the solvents and catalysts disclosed above for the acrylated maleurates.

The allyl and methallyl derivatives are prepared by reacting NCMI, NCCI or NCII with the corresponding alcohols or amines under conditions described above for the acrylated maleurate monomers. Examples of suitable alcohols and amines include allyl alcohol, methallyl alcohol, allylamine, methallylamine, diallylamine and dimethallylamine.

The trans isomers of the monomers of this invention are prepared by isomerizing the corresponding cis isomers by heating in the presence of catalysts including acids such as hydrochloric and sulfuric acids, $AlCl_3$, pyridine, etc., preferably in a solvent such as acetonitrile, 1,2-dimethoxyethane, etc.

A preferred method for preparing the maleurate monomers is a one-pot procedure, wherein urea and maleic anhydride are reacted in a non-reactive polar organic solvent including, for example, acetonitrile, acetone, methyl ethylketone and acetic acid. The preferable non-reactive polar organic solvents are acetonitrile and acetic acid, more preferably acetic acid. The reaction of urea and maleic anhydride in the non-reactive polar organic solvent, for example, in acetic acid, is conducted at 50°–100° C., preferably 60°–80° C. to form the maleuric acid intermediate, which has an open ring structure. The reaction is typically complete in about 4–10 hours depending on the reaction temperature employed. A dehydrating agent is then added to the reaction mixture which is heated for another 2 to 4 hours at the same temperature range indicated above to cyclize maleuric acid to NCMI. Suitable dehydrating agents, include, for example, acetic anhydride, propionic anhydride and butyric anhydride. The non-reactive polar organic solvent (i.e., acetic acid) of NCMI is then reacted in the same pot with the appropriate hydroxyl coreactant to form the maleurate monomers as solutions in the non-reactive polar organic solvent (i.e., acetic acid). As disclosed hereinabove, the reaction of NCMI with the hydroxyl compounds may be accelerated by incorporating into the reaction mixture suitable catalysts as, for example, zinc acetate. For end use applications the monomers may be used without isolation. However, if desired, the non-reactive polar organic solvent (i.e., acetic acid) may be removed under vacuum or the reaction mixture may be diluted with water to precipitate the monomers which can be dried and dissolved in other suitable solvents or comonomers such as methyl methacrylic acid, methacrylic acid and/or acrylic acid.

The maleurate esters and amides of hydroxyethylethylene urea and aminoethylethylene urea can also be obtained by the same one-pot process described above. However, these monomers are water soluble and thus cannot be precipitated by adding water to the non-reactive polar organic solvent (i.e., acetic acid) solution. Instead, they can be used in the non-reactive polar organic solvent or the non-reactive polar organic solvent (i.e., acetic acid) can be removed by vacuum stripping and the resulting monomers may be dissolved in water and/or methacrylic acid and its mixtures with other comonomers.

The citraconurates, itaconurates and the corresponding amides may similarly be prepared by the one-pot process described above using NCSI, NCCI or NCII, respectively, instead of NCMI.

Preparation of Maleuric, Citraconuric, and Itaconuric Acids and Their Alkyl Esters Maleuric, citraconuric and itaconuric acids are prepared by a known procedures as those, for example, described in U.S. Pat. Nos. 2,717,908 and 2,788,349 which are herein incorporated by reference for all purposes as if fully set forth. By way of example, maleuric acid is prepared by reacting maleic anhydride and urea in a solvent such as acetic acid or acetonitrile. The alkyl maleurates succinurates, citraconurates and itaconurates are prepared by reacting NCMI, NCCI or NCII with alcohols such as methanol, propanol, isopropanol, butanol, lsobutanol, octanol, octadecanol, dodecanol, etc., by procedures well-known to those skilled in the relevant art. Fumauric acid and its alkyl esters are prepared by isomerizing maleuric acid and its alkyl esters by heating in the presence of catalysts including pyridine and aluminum chloride and following procedures known to those skilled in the art.

Glyoxylation

Glycomaleurates, glycofumaurates, glycomaleuramides, glycofumauramides, glycocitraconurates, glycoitaconurates, glycocitraconuramides, glycoitaconuramides are prepared by glyoxylation of the precursor maleurates, fumaurates, maleuramides, fumauramides, citraconurates, itaconurates, citraconuramides and itaconuramides from step above by heating these compounds with glyoxal in refluxing water, dioxane or mixtures thereof. Other suitable co-solvents include acetonitrile, dimethoxyethane and tetrahydrofuran. The preferred pH range for the glyoxylation reaction is 7.0–7.5. in most cases, the pH of the commercial 40% aqueous glyoxal (2.0–3.5) is adjusted with aqueous saturated sodium bicarbonate to the preferred range. The reaction results in relatively high yields of the desired glyoxylated acyl imidazolidinone monomers.

The glyoxylated monomers are etherified by heating these with alcohols, optionally in the presence of an acid catalyst. Suitable alcohols include methanol, ethanol, isopropanol, propanol, butanol, octanol and the like. Suitable catalysts include $H_2SO_4$ and hydrochloric acid and supported acid catalysts. All of the above monomers may also be methylolated by subsequent reaction with formaldehyde. If the methylolation reaction is carried out in the presence of an alcohol, alkoxymethyl derivatives are produced.

The Novel Acyl Imidazolidinone Monomers

The acyl imidazolidinone monomers of this invention are glyoxylated derivatives of alkyl, allyl, acrylic and cyclic urea maleurates, fumaurates, maleuramides, fumauramides, citraconurates, citraconuramides, itaconurates and itaconuramides of the general Formula (I) above. As shown above, the novel compounds of the invention also include glyoxylated maleuric acid, fumauric acid, citraconuric acid and itaconuric acid. A preferred embodiment for the present invention are those compounds represented by the Formula (I), wherein A is O, Y is —CH=CH— and R is represented by the formula

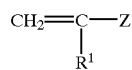

wherein Z is independently selected from

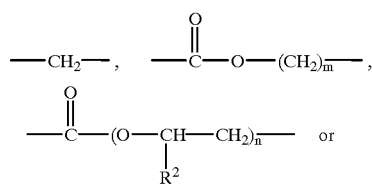

-continued

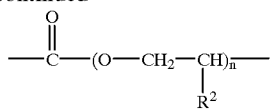

More preferred are monomers wherein Z is —COO(CH$_2$)$_m$—, and m is 2. As examples may be mentioned the preparation of polymerizable monomers from the reaction of butyl maleurate, hydroxyethyl methacrylate fumaurate and hydroxyethylethylene urea maleurate with glyoxal which yield novel compositions of the chemical structures shown below:

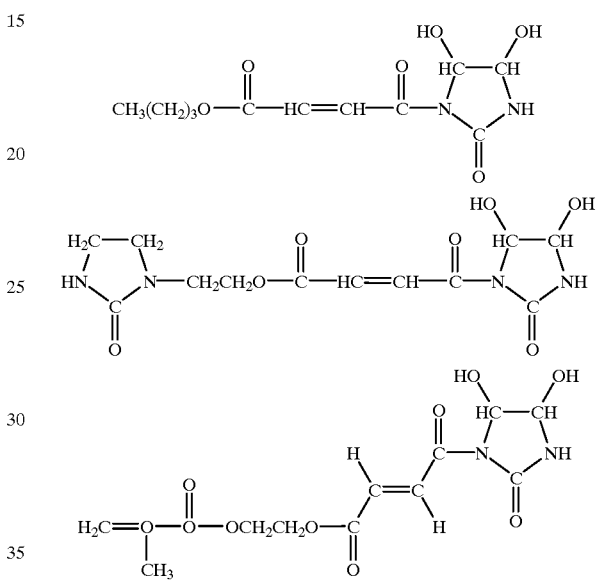

Uses of Novel Polymerizable Monomers

The novel polymerizable acyl imidazolidinone monomers in accordance with the present invention are self-crosslinking which allows for their use in the preparation of self-crosslinking polymers. The acyl imidazolidinone monomers find use, for example in latex applications, pigment binders, nonwovens, adhesives, coatings, caulks, sealants, paper sizing, wet and dry strength resins and textile applications. The acyl imidazolidinone monomers may also be used as wet adhesion promoters. When employed as paper sizing agents, the concentrations of the novel monomers may range from about 0.1% to about 3.0% based on the monomer mixture.

Specifically the acyl imidazolidinone monomers may be used as comonomers in monomer systems for forming aqueous emulsion polymers, including in compositions comprising monomers such as acrylics, vinyls, vinyl aromatics, α,β-unsaturated carboxylic acids and their esters, as well as other known specialty monomers.

Examples of suitable acrylic monomers include methyl acrylate, methyl methacrylate, hydroxyalkyl acrylate, hydroxyalkyl methacrylate, butyl acrylate, hexyl acrylate, cyclohexyl acrylate, 2-hydroxyethyl mothacrylate, 2-hydroxyethyl acrylate, 2-hydroxypropyl methacrylate, 2-hydroxypropyl acrylate, piperidinoethyl methacrylate, morpholinoethyl methacrylate, and the like.

Examples of suitable vinyl monomers include ethylene, propylene, butylene, isobutylene, hexene, vinyl acetate, vinyl chloride, acrylonitrile, vinylidene chloride, oleic acid, linoleic acid, 1,3-butadiene, isoprene, norbornene, cyclopentadiene and the like.

Examples of useful unsaturated dicarboxylic acids include itaconic acid, cinnamic acid, crotonic acid, mesaconic acid, maleic acid, fumaric acid, and the like; alpha, beta unsaturated dicarboxylic acid esters of the dicarboxylic acid esters described above including aromatic esters, cycloalkyl esters, alkyl esters, hydroxyalkyl esters, alkoxy alkyl esters, and the like.

Examples of suitable vinyl aromatic monomers with which the present invention's monomers can be polymerized include styrene, α-methylstyrene, vinyltoluene, ethylstyrene, isopropylstyrene, p-hydroxystyrene, p-acetoxystyrene, and p-chlorostyrene.

In particular, the novel acyl imidazolidinone monomers of this invention may be incorporated in effective amounts in aqueous polymer systems such as vinyl and acrylic acid latex polymer systems to act as self-crosslinking components. The emulsion polymers used in formulating latex paints usually are all acrylic copolymers comprising alkyl esters of acrylic and methacrylic acid with minor amounts of acrylic and methacrylic acid, or they are vinyl/acrylic polymers comprising vinyl containing monomers or polymers in combination with softer acrylic monomers. The commonly used ethylenically unsaturated monomers in making acrylic paints are butyl acrylate, methyl methacrylate, ethyl acrylate and mixtures thereof. In acrylic paint compositions at least 50% of the polymer formed is comprised of an ester of acrylic or methacrylic acid. The vinyl-acrylic paints usually include ethylenically unsaturated monomers such as vinyl acetate and butyl acrylate or 2-ethylhexyl acrylate. In vinyl acrylic paint compositions, at least 50% of the polymer formed is comprised of vinyl acetate, with the remainder being selected from the esters of acrylic or methacrylic acid.

The novel monomers of this invention may be added to the monomer composition from which acrylic or vinyl acrylic polymers are formed in a concentration which may vary over a wide range. Preferably the concentration is at least sufficient to improve the wet adhesion of paints made from the polymer composition. Concentrations may range from about 0.05% to about 20%, by weight, based on the total weight of the monomers. Preferably, the concentration is in the range of from about 0.1% to about 5.0%, and more preferably from about 0.5% to about 3.0%.

The monomer composition may be used in conjunction with other ingredients, such as various free radical catalysts to initiate polymerization, emulsifying agents to protect particles from agglomeration, and buffers to maintain a desired pH during polymerization, as is generally well-known to those of ordinary skill in the art of polymerization. For example, suitable free radical polymerization catalysts are the catalysts known to promote emulsion polymerization and include water-soluble oxidizing agents such as organic peroxides (e.g., t-butyl hydroperoxide, cumene hydroperoxide, etc.), inorganic oxidizing agents (e.g., hydrogen peroxide, potassium persulfate, sodium persulfate, ammonium persulfate, etc.) And those catalysts that are activated in the water phase by a water-soluble reducing agent. Such catalysts are employed in a catalytic amount sufficient to cause polymerization. Generally, a catalytic amount ranges from about 0.01 to 5.0 parts per hundred parts of monomer. As alternatives to heat and catalytic compounds to activate polymerization, other free radical producing means, such as exposure to activating radiations, can be employed.

Suitable emulsifying agents include anionic, cationic, and nonionic emulsifiers customarily used in emulsion polymerization. Usually, at least one anionic emulsifier is utilized and one or more nonionic emulsifiers may also be utilized. Representative anionic emulsifiers are the alkyl aryl sulfonates, alkali metal alkyl sulfates, the sulfonated alkyl esters and fatty acid soaps. The emulsifying agents are employed in amounts to achieve adequate emulsification and to provide desired particle size and particle size distribution.

Examples of suitable buffers used to maintain a desired pH during polymerization include ingredients such as acids, salts, chain transfer agents and chelating agents. For example, if the polymerization constituents include a monoethylenically unsaturated carboxylic acid comonomer, polymerization under acidic conditions (pH 2–7, preferably 2–5) is preferred. In such instances, the aqueous medium can include those known weak acids and their salts that are commonly used to provide a buffered system at the desired pH range.

The manner of combining the polymerization ingredients can be various known monomer feed methods, such as, continuous monomer addition, incremental monomer addition, or addition in a single charge of the entire amount of monomers. The entire amount of the aqueous medium with polymerization additives can be present on the polymerization vessel before introduction of the monomer, or alternatively, the aqueous medium, or a portion of it, can be added continuously or incrementally during the course of the polymerization.

The polymerization of the monomer system which includes ethylenically unsaturated monomers and either one or more of the the novel acyl imidazolidinone monomers of the present invention can be accomplished by known procedures for polymerization in aqueous emulsions, as disclosed, for example, in U.S. Pat. Nos. 3,366,613, 4,104, 220, 2,881,171 and 4,219,452, and EP-A-0626672, which are incorporated by reference herein for all purposes as if fully set forth. Pre-polymer monomeric starting materials used to form polymeric pre-emulsion compositions using the monomers of the present invention are typically dissolved or suspended in the aqueous medium to a desired concentration. Preferably, the polymerization of the invention is performed at a concentration range of about 10 weight-% to about 70 weight-% of the monomers in the aqueous medium, although somewhat higher or lower concentrations may be employed in some cases.

By way of example, polymerization is initiated by heating the emulsified mixture with continued agitation to a temperature usually between about 50° C. to about 110° C., preferably between 60° C. to about 100° C. Heating of the emulsified mixture is also preferably conducted in an inert atmosphere (e.g., purging with nitrogen, argon, etc.). Polymerization is continued by maintaining the emulsified mixture at the desired temperature until conversion of the monomer or monomers to polymer has been reached.

Generally, depending upon the final application of the polymeric composition, the polymer may contain anywhere from about 0.05 weight-% to about 20.0 weight-% of the monomer of the present invention, preferably from about 0.1% to about 5.0% weight-% of the present monomer, and more preferably from about 0.5% to about 3.0 weight-% of the monomer of the present invention.

In addition to making emulsion polymers, it is contemplated that the monounsaturated reaction products and compounds of the present invention be used to form solution copolymers. Polymerization towards the formulation of solution polymers may be completed under substantially similar circumstances as described above for emulsion polymerization except that the medium of polymerization in a solution polymerization reaction is organic instead of aqueous. Generally, the solution polymerization reaction is carried out with the monomers in solution in an inert organic solvent such as tetrahydrofuran, methyl ethyl ketone, acetone, ethyl acetate, or other suitable organic solvents such as hexane, heptane, octane, toluene, xylene and mixtures thereof. In the case of water-soluble monomers, inverse emulsions may also be prepared. Inverse emulsions being defined as a water-soluble polymer system dispersed in an organic solvent. Preferred solvents are non-toxic and odorless.

The invention will now be illustrated by the following examples. The examples are not intended to be limiting of the scope of the present invention. In conjunction with the general and detailed descriptions above, the examples provide further understanding of the present invention.

EXAMPLE A

Maleuric Acid

Maleuric acid was prepared according to the procedure of U.S. Pat. No. 2,717,908. A mixture of 500 g of maleic anhydride (5.1 moles) and 300 g of urea (5 moles) in 1000 mL of acetic acid was heated to 50° C. The mixture was a homogeneous solution until maleuric acid began to precipitate out. After 12 hours, the mixture was cooled to room temperature overnight. The maleuric acid was filtered and washed with acetic acid to afford 530 g (67% yield). Additional maleuric acid precipitates from the mother liquor over time to afford nearly a quantitative yield.

$^1$H NMR (DMSO-$d_6$): δ12.8 (brs, 1H), 10.4 (brs, 1H), 7.6 (brs, 1H), 7.3 (brs, 1H), 6.4 (s, 2H).

EXAMPLE B

N-Carbamylmaleimide

N-carbamylmaleimide was also prepared according to the procedure of U.S. Pat. No. 2,788,349. A total of 500 g of maleuric acid was added to 1.5 L of acetic anhydride heated to 85° C. After 30 minutes, the mixture became homogeneous. After an additional 1 hour, the solution was cooled to room temperature. The precipitated N-carbamylmaleimide was filtered and washed with acetone to afford 405 g (90% yield). $^1$H NMR (DMSO-$d_6$): δ7.8 (br s, 1H), 7.4 (br s, 1H), 7.1 (s, 2H); $^{13}$C NMR (DMSO-$d_6$): δ169, 148, 135.

EXAMPLE C

Butyl Maleurate

A mixture of 140 g of N-carbamylmaleimide (1 mole), 1.36 g of zinc chloride (0.01 moles) and 150 g of n-butanol (2 moles) was heated to reflux. After 4 hours, the mixture was poured into 400 mL of water and cooled to room temperature. The butyl maleurate was filtered, washed with water and dried to afford 200 g (93% yield). M.P.: 97°–90° C.; $^1$H NMR (CDCl$_3$): δ10.6 (brs, 1H), 8.2 (brs, 1H), 6.3 (AB, 2H), 5.9 (brs, 1H), 4.2 (t, 2H), 1.6 (m, 2H), 1.4 (m, 2H), 0.9 (t, 3H); HPLC (20 to 40% CH$_3$CN/H$_2$O over 20 minutes, C$_8$): R$_t$=9.4 minutes.

EXAMPLE D

Methyl Maleurate

A mixture of 10 g of N-carbamylmaleimide (0.071 moles) in 40 mL of methanol was heated to reflux. After 6 hours, the excess methanol was evaporated to afford 11.5 g (93% yield) of methyl maleurate. M.P.: 112°–14° C.; $^1$H NMR (CDCl$_3$): δ10.4 (br s, 1H), 8.2 (br s, 1H), 6.3 (m, 2H), 5.6 (br s,1H), 3.8 (s, 3H); HPLC (5% CH$_3$CN/H$_2$O, C$_8$): R$_t$=6.3 minutes.

EXAMPLE E

Isopropyl Maleurate

The addition of isopropanol to N-carbamylmaleimide under the conditions of Example C afforded a 95% yield of isopropyl maleurate. M.P.: 113°–14° C.; $^1$H NMR (CDCl$_3$): δ10.6 (br s, 1H), 8.2 (br s, 1H), 6.3 (AB, 2H), 5.8 (br s, 1H), 5.2 (quintet, 1H), 1.3 (d, 6H); HPLC (20% CH$_3$CN/H$_2$O, C$_8$): R$_t$=5.6 minutes.

EXAMPLE F

2-Ethylhexyl Maleurate

The addition of 2-ethylhexanol to N-carbamylmaleimide under the conditions of Example C afforded a 95% yield of 2-ethylhexyl maleurate. M.P.: 73°–6° C.; $^1$H NMR (CDCl$_3$): δ10.6 (br s, 1H), 8.2 (br s, 1H), 6.3 (m, 2H), 5.8 (br s, 1H), 4.2 (m, 2H), 1.6 (m, 1H), 1.3 (m, 8H), 0.9 (t, 6H); HPLC (40% CH$_3$CN/H$_2$O, C$_8$): R$_t$=14.2 minutes.

EXAMPLE G

Hexadecyl Maleurate

A mixture of 49 g of hexadecanol (0.202 moles), 28 g of N-carbamylmaleimide (0.2 moles) and 270 mg of zinc chloride (0.002 moles) in 300 mL of p-dioxane was heated to reflux. After 24 hours, the mixture was cooled to room temperature and 200 mL of H$_2$O was added. The resulting solid was filtered, washed with additional H$_2$O and dried to afford 75 g (97% yield) of hexadecyl maleurate. M.P.: 106°–09° C. (dec.); $^1$H NMR (CDCl$_3$): δ10.5 (br s, 1H), 8.2 (br s, 1H), 6.3 (m, 2H), 5.4 (br s, 1H), 4.2 (t, 2H), 1.6 (m, 2 H), 1.2 (m, 26H), 0.9 (t, 3H); HPLC (80% CH$_3$CN/H$_2$O, C$_{18}$): R$_t$=6.9 minutes.

EXAMPLE H

Octadecyl Maleurate

The addition of octadecanol to N-carbamylmaleimide under the conditions of Example G afforded a 97% yield of octadecyl maleurate. M.P.: 109°–11° C. (dec.); $^1$H NMR (CDCl$_3$): δ10.5 (brs, 1H), 8.2 (br s, 1H), 6.3 (m, 2H), 5.4 (br s, 1H), 4.2 (t, 2H), 1.6 (m, 2H), 1.2 (m, 30H), 0.9 (t, 3H); HPLC (80% CH$_3$CN/H$_2$O, C$_{18}$): R$_t$=12.8 minutes.

EXAMPLE I

Allyl Maleurate

A mixture of 2.96 g of allyl alcohol (0.051 moles), 7 g of N-carbamylmaleimide (0.05 moles) and 110 mg of zinc acetate dihydrate (0.0005 moles) in 20 mL of acetonitrile was heated to reflux. After 8 hours, the acetonitrile was evaporated. The solid was washed with H$_2$O and dried to afford 9.9 g (99% yield) of allyl maleurate. M.P.: 108°–10° C.; $^1$H NMR (DMSO-$d_6$): δ10.5 (br s, 1H), 7.6 (br s, 1H), 7.3 (br s, 1H), 6.5 (AB, 2H), 5.9 (m, 1H), 5.3 (d of d, 1H), 5.2 (d of d, 1H), 4.6 (d, 2H); HPLC (10% CH$_3$CN/H$_2$O, C$_{18}$): R$_t$=4.9 min.

EXAMPLE J

2-Hydroxyethyl Acrylate Maleurate

A mixture of 140 g of N-carbamylmaleimide (1 mole), 121.8 g of 2-hydroxyethyl acrylate (1.05 moles) and 1.36 g of zinc chloride (0.01 moles) in 200 mL of acetonitrile was heated to reflux. After 5 hours, the mixture was poured into 500 mL of water. The solid was filtered, washed with water and dried to afford 240.7 g (94% yield) of 2-hydroxyethyl acrylate maleurate. M.P.: 88°–90° C. (dec.); $^1$H NMR (CDCl$_3$): δ10.4 (br s, 1H), 8.2 (br s, 1H), 6.4 (m, 3H), 6.2 (d of d, 1H), 5.9 (m, 2H), 4.4 (A$_2$B$_2$, 4H); $^{13}$C NMR (CDCl$_3$): δ165.9, 165.3, 165.2, 155.1, 133.1, 131.6, 129.5, 127.8, 63.2, 61.9; HPLC (10% CH$_3$CN/H$_2$O, C$_{18}$): R$_t$=5.7 minutes.

EXAMPLE K

2-Hydroxyethyl Methacrylate Maleurate

A mixture of 140 g of N-carbamylmaleimide (1 mole), 130 g of 2-hydroxyethyl methacrylate (1 mole) and 1.36 g of zinc chloride (0.01 moles) in 200 mL of acetonitrile was heated to reflux. After 6 hours, the acetonitrile was evaporated and 500 mL of H$_2$O was added. The solid was filtered and dried to afford 200 g (74% yield) of 2-hydroxyethyl methacrylate maleurate. M.P.: 62°–4° C. (dec.); $^1$H NMR (CDCl$_3$): δ10.5 (br s, 1H), 8.2 (br s, 1H), 6.4 (m, 2H), 6.1 (m, 1H), 5.8 (br s, 1H), 5.6 (m, 1H), 4.4 (A$_2$B$_2$, 4H), 2.0 (m, 3H); $^{13}$C (CDCl$_3$): δ167.1, 165.24, 165.23, 155.1, 135.8, 132.9, 129.6, 126.2, 63.2, 62.0, 18.2; HPLC (20% CH$_3$CN/H$_2$O, C$_{18}$): R$_t$=3.5 minutes.

EXAMPLE L

Hydroxyethylethyleneurea

A mixture of 93.3 g of 2-(2-aminoethylamino)ethanol (0.9 moles) and 52.1 g of urea (0.87 moles) was heated slowly to 230° C. with stirring. The evolution of ammonia began when the temperature reached 130° C. The reaction mixture was heated at 230° C. for 2 hours. The mixture solidified to a light-yellow solid after it had cooled to room temperature to afford 110.5 g of hydroxyethylethyleneurea. Recrystallized from acetone, M.P.: 55–57.5° C.; $^1$H NMR (DMSO-d$_6$): δ6.3 (s, 1H), 4.6 (s, 1H), 3.5–3.0 (m, 8H).

EXAMPLE M

Maleurate Ester of Hydroxyethylethyleneurea

A mixture of 3 g of hydroxyethylethyleneurea (0.023 moles), 3.2 g of N-carbamylmaleimide (0.023 moles), 0.15 g of zinc acetate (0.0007 moles) was refluxed in 25 mL of acetonitrile. After 6 hours, the reaction mixture was cooled to room temperature and the acetonitrile was evaporated to afford 6.2 g of hydroxyethylethyleneurea maleurate as a tan solid. $^1$H NMR (DMSO-d$_6$): δ10.5 (s, 1H), 7.6 (s, 1H), 6.4 (s, 2H), 6.3 (s, 1H), 4.2 (t, 1H), 3.4 (t, 3H), 3.1–3.3 (m, 4H).

EXAMPLE N

Isomerization of 2-hydroxyethyl Methacrylate Maleurate to the Fumaurate

A mixture of 8.1 g of 2-hydroxyethyl methacrylate maleurate and 0.81 g of sulfuric acid in 45 mL of acetonitrile was heated to reflux. After 12 hours, the mixture was cooled to room temperature and H$_2$O was added. The mixture was filtered, washed with H$_2$O and dried to afford 7.1 g (87% yield) of the fumaurate. M.P.: 135°–38° C.; $^1$H NMR (DMSO-d$_6$): δ10.6 (br s, 1H), 7.7 (brs, 1H), 7.4 (br s, 1H), 7.2 (d, 1H), 6.8 (d, 1H), 6.0 (m, 1H), 5.7 (m, 1H), 4.4 (A$_2$B$_2$, 4H), 1.9 (m, 3H); HPLC (20% CH$_3$CN/H$_2$O, C$_{18}$): R$_t$=7.7 minutes. HPLC analysis of the mother liquor indicated a mixture of the maleurate (R$_t$=3.7 minutes) and the fumaurate.

EXAMPLE O

Citraconuric Acid

Citraconuric acid was prepared according to the procedure of U.S. Pat. No. 2,717,908, A mixture of 286 g of citraconic anhydride (2.55 moles) and 150 g of urea (2.5 moles) in 500 mL of acetic acid was heated to 50° C. After 12 hours, the mixture was cooled to room temperature overnight. Most of the acetic acid was evaporated. The citraconuric acid was filtered and washed with acetic acid to afford 215 g (50% yield).

EXAMPLE P

N-Carbamylcitraconimide

N-Carbamylcitraconimide was prepared according to the procedure of U.S. Pat. No. 2,788,349. A total of 167 g of citraconuric acid (0.97 moles) was added to 500 mL of acetic anhydride heated to 85° C. After 30 minutes, the mixture became homogeneous. After an additional 1 hour, the solution was cooled to room temperature. The precipitated N-carbamylcitraconimide was filtered and washed with acetone to afford 105 g (70% yield).

EXAMPLE Q

Itaconuric Acid

Itaconuric acid was prepared according to the procedure of U.S. Pat. No. 2,717,908. A mixture of 123 g of itaconic anhydride (1.1 moles) and 60 g of urea (1 mole) in 200 mL of acetic acid was heated to 50° C. After 12 hours, the mixture was cooled to room temperature overnight. Most of the acetic acid was evaporated. The itaconuric acid was filtered and washed with acetic acid to afford 51 g (30% yield).

EXAMPLE R

N-Carbamylitaconimide

N-carbamylitaconimide was prepared according to the procedure of U.S. Pat. No. 2,788,349. 30 g of itaconuric acid (0.17 moles) was added to 100 mL of acetic anhydride heated to 85° C. After 30 minutes, the mixture became homogeneous. After an additional 1 hour, the solution was cooled to room temperature. The precipitated N-carbamylitaconimide was filtered and washed with acetone to afford 16 (60% yield).

EXAMPLE S

Octadecyl Citraconurate

A mixture of 27.6 g of octadecanol (0.101 moles), 15.4 g of N-carbamylcitraconimide (0.1 mole) and 135 mg of zinc chloride (0.001 moles) in 150 mL of p-dioxane was heated to reflux. After 24 hours, the mixture was cooled to room temperature and 100 mL of H$_2$O added. The resulting solid was filtered, washed with additional H$_2$O and dried to afford nearly a quantitative yield of octadecyl citraconurate.

EXAMPLE T

Octadecyl Itaconurate

A mixture of 5.47 g of octadecanol (0.02 moles), 3.08 g of N-carbamylitaconimide (0.02 moles) and 27.0 mg of zinc chloride (0.0002 moles) in 30 mL of p-dioxane was heated to reflux. After 24 hours, the mixture was cooled to room temperature and 20 mL of $H_2O$ added. The resulting solid was filtered, washed with additional $H_2O$ and dried to afford nearly a quantitative yield of octadecyl itaconurate.

EXAMPLE U

Octadecyl Fumaurate

A mixture of 8.2 g of octadecyl maleurate (0.02 mole) was isomerized to the trans isomer according to the procedure of Example R. The isolated yield of the desired octadecyl fumaurate was 7.4 g (88.5%).

Glyoxylated Monomers

EXAMPLE 1

Butyl Maleurate Plus Glyoxal

Monomer M1

The pH of 36.25 g of 40% glyoxal (0.25 moles) was adjusted to 7.1 with aqueous saturated sodium bicarbonate. A mixture of 53.55 g of butyl maleurate (Example C) (0.25 moles) and 200 mL of water were added and the mixture was heated to reflux. After 4 hours, the water was evaporated and 300 mL of acetone and a few grams of decolorizing charcoal were added. The mixture was filtered and the filtrate evaporated to afford 47.9 g (70% yield) of the addition product as a yellow-orange viscous syrup. $^1H$ NMR ($D_2O$): $\delta 7.0$ (m, 1H), 6.2 (m, 1H), 5.6(s,1H), 5.1 (s, 1H), 4.2 (m, 2H), 1.6 (m, 2H), 1.4 (m, 2H), 0.9 (t, 3H), HPLC (20% to 40% $CH_3CN/H_2O$ (20 minutes), $C_8$): $R_t$=6.7 minutes.

EXAMPLE 2

Maleuric Acid Plus Glyoxal

Monomer M2

The addition of glyoxal to maleuric acid under the conditions of Example 1 afforded a 1:1 mixture (molar basis, determined by integration of the proton NMR spectrum) of addition product and maleuric acid with a 90% material balance. $^1H$ NMR ($D_2O$): $\delta 7.0$ (d, 1H), 6.3 (d, 1H), 5.6 (s, 1H), 5.1 (s, 1H), maleuric acid at $\delta 6.4$ (s); HPLC (100% $H_2O$, $C_8$): the product and maleuric acid co-elute at $R_t$=1.2 minutes.

EXAMPLE 3

Methyl Maleurate Plus Glyoxal

Monomer M3

The addition of glyoxal to methyl maleurate under the conditions of Example 1 afforded a 2:1 mixture of addition product and maleuric acid (due to hydrolysis of the ester) with a 95% material balance. $^1H$ NMR ($D_2O$): $\delta 7.0$ (d, 1H), 6.2 (d, 1H), 5.6 (s, 1H), 5.1 (s, 1H), 3.8 (s, 3H), maleuric at $\delta 6.4$ (s); HPLC (5% $CH_3CN/H_2O$, $C_8$): $R_t$=4.1 and 1.2 (maleuric acid) minutes.

EXAMPLE 4

Isopropyl Maleurate Plus Glyoxal

Monomer M4

The addition of glyoxal to isopropyl maleurate under the conditions of Example 1 afforded a 94% yield of the addition product. $^1H$ NMR ($D_2O$): $\delta 7.0$ (d, 1H), 6.2 (d, 1H), 5.6 (s, 1H), 5.1 (s, 1H), 5.0 (m, 1H), 1.2 (d, 6H); HPLC (20% $CH_3CN/H_2O$, $C_{18}$): $R_t$=2.9 minutes.

EXAMPLE 5

Allyl Maleurate Plus Glyoxal

Monomer M5

The addition of glyoxal to allyl maleurate under the conditions of Example 1 afforded a 67% yield of the addition product. $^1H$ NMR ($D_2O$): $\delta 7.0$ (d, 1H), 6.3 (d, 1H), 5.95 (m, 1H), 5.6 (s, 1H), 5.3 (d of d of d, 2H), 5.1 (s, 1H), 4.7 (d, 2H); HPLC (10% $CH_3CN/H_2O$, $C_{18}$): $R_t$=2.9 minutes.

EXAMPLE 6

2-Ethylhexyl Maleurate Plus Glyoxal

Monomer M6

The pH of 43.5 g of 40% glyoxal (0.3 moles) was adjusted to 7.1 with aqueous saturated sodium bicarbonate. A mixture of 27 g of 2-ethylhexyl maleurate (0.1 moles) and 300 mL of p-dioxane were added and heated to reflux. After 4 hours, the dioxane was evaporated and ethyl acetate and water were added to the crude product. The aqueous layer was extracted with additional ethyl acetate. The combined organic layers were dried with magnesium sulfate, filtered and evaporated to afford 30 g (91% yield) of the addition product as a viscous yellow syrup. $^1H$ NMR ($CDCl_3$): $\delta 6.9$ (m, 1H), 6.2 (m, 1H), 5.0–5.8 (m, 4H), 4.0 (m, 2H), 1.6 (m, 1H), 1.3 (m, 8H), 0.9 (m, 6H); HPLC (40% $CH_3CN/H_2O$, $C_8$): $R_t$=9.0 minutes.

EXAMPLE 7

Hexadecyl Maleurate Plus Glyoxal

Monomer M7

The addition of glyoxal to hexadecyl maleurate under the conditions of Example 6 afforded a 95% yield of the addition product after precipitation of the reaction mixture from water. M.P.: 64°–8° C. (dec.); $^1H$ NMR ($CDCl_3$): $\delta 6.9$ (m, 1H), 6.1 (m, 1H), 5.0–5.8 (m, 4H), 4.0 (m, 2H), 1.6 (m, 2H), 1.2 (m, 26H), 0.9 (t, 3H); HPLC (80% $CH_3CN/H_2O$, $C_{18}$): $R_t$=4.5 minutes.

EXAMPLE 8

Octadecyl Maleurate Plus Glyoxal

Monomer M8

The addition of glyoxal to octadecyl maleurate under the conditions of Example 6 afforded a 95% yield of the addition product after precipitation of the reaction mixture from water. The crude product was an 8:2:1 mixture of addition product, octadecyl maleurate and octadecanol. $^1H$ NMR ($CDCl_3$): $\delta$addition product 6.9 (m, 1H), 6.1 (m, 1H), 5.6 (s, 1H), 5.0 (s, 1H), 4.1, 1.6, 1.2, 0.9, octadecylmaleurate $\delta 6.3$, 4.2, 1.6, 1.2, 0.9, octadecanol $\delta 3.6$, 1.6, 1.2, 0.9; HPLC (80% $CH_3CN/H_2O$, $C_{18}$): $R_t$=8.2 minutes.

EXAMPLE 9

Octadecyl Citraconurate Plus Glyoxal

Monomer M9

The addition of glyoxal to octadecyl citraconurate under the conditions of Example 6 afforded a similar product distribution as Example 8 upon precipitation of the reaction mixture from water.

EXAMPLE 10

Octadecyl Itaconurate Plus Glyoxal

Monomer M10

The addition of glyoxal to octadecyl itaconurate under the conditions of Example 6 afforded a similar product distribution as Example 8 upon precipitation of the reaction mixture from water.

EXAMPLE 11

2-Hydroxyethylacrylate Maleurate Plus Glyoxal

Monomer M11

The addition of glyoxal to 2-hydroxyethylacrylate maleurate under the conditions of Example 1 (pH 7.2 and 4) and Example 6 afforded a 1:1:1 mixture of maleuric acid, 2-hydroxyethylacrylate and addition product. $^1$H NMR ($D_2O$) diagnostic peaks: addition product $\delta$5.6 and 5.0, 2-hydroxyethylacrylate $\delta$4.2 and 3.8, maleuric acid $\delta$6.4;HPLC (10% $CH_3CN/H_2O$, $C_{18}$ Novapak column): $R_t$=1.4 minutes (M+H=117 and 159), 10 minutes (M+H=315), 2-hydroxyethylacrylate maleurate elutes at 8 minutes.

EXAMPLE 12

2-Hydroxyethyl Methacrylate Fumaurate Plus Glyoxal

Monomer M12

A mixture of 2.7 g of 2-hydroxyethyl methacrylate fumaurate (0.01 moles) and 1.45 g of 40% aqueous glyoxal (0.01 moles), neutralized to pH 7 with aqueous saturated sodium bicarbonate, in 20 mL of $H_2O$ was heated to reflux. After 24 hours, the mixture was cooled to room temperature and the solids filtered. HPLC analysis of the solids indicated mostly starting material (with some addition product). 610 mg was isolated (22% recovery of starting material). Concentration of the aqueous filtrate led to partial polymerization. The product is stable as an aqueous solution. $^1$H NMR ($D_2O$): $\delta$8.0 (d, 1H), 6.8 (d, 1H), 6.1 (m, 1H), 5.7 (m, 1H), 5.6 (s, 1H), 5.0 (s, 1H), 4.5 (m, 4H), 1.9 (m, 3H); HPLC (20% $CH_3CN/H_2O$, $C_{18}$): $R_t$=4.4 minutes.

EXAMPLE 13

Glyoxylated Butyl Maleurate Plus Methanol

Monomer 13

Butyl maleurate was reacted with excess methanol at reflux in the presence of an acid catalyst (Amberlys® sulfonic acid resin). Evaporation of the excess methanol afforded a monomethoxy glycomaleurate as determined by LC-MS analysis (MH at m/z=287) in approximately 50% yield. Dimethylmaleate was identified as one of the side products (MH at m/z=145).

EXAMPLE 14

Hydroxyethylethyleneurea Maleurate Plus Glyoxal

Monomer M14

3.4 g of 40% aqueous glyoxal (0.023 moles) was neutralized with saturated aqueous sodium bicarbonate until the pH was 7.2. A mixture of 6.5 g of hydroxyethylethyleneurea maleurate (0.024 moles) and 20 mL of water were added and heated to reflux. After 4 hours, the water was evaporated to afford 7.5 g of an orange solid. M.P.: 60°–6° C.; IR (Nujol): 3300, 1720, 1680, 1500, 1260, 1070 $cm^{-1}$.

EXAMPLE 15

Octadecyl Glycofumaurate

Monomer M15

The addition of glyoxal to 4.1 g of octadecyl fumaurate under the conditions of Example 6 afforded 3.9 g of the product which had a purity of about 95%.

Self-Crosslinking Latexes

Vinyl-Acrylic Latex

The examples below describe the preparation of vinyl-acrylic and all acrylic latexes containing the glyoxylated compounds of the present invention. They also describe their evaluation as self-crosslinking polymers for use in non-woven and other binder applications.

EXAMPLE 16

A. Latex Preparation Using Glyoxylated Butyl Maleurate (Butyl Glycomaleurate, Monomer)

A 500 mL five-neck flask equipped with a thermometer, condenser, agitator, addition funnel and a gas inlet tube was charged with 100 g of distilled water, 0.5 9 of 23% sodium dodecylbenzene sulfonate, 0.6 g of 20% ethoxylated alkylphenol (GAF IGEPAL CA-620), 0.13 g of sodium acetate and 0.2 g of ammonium persulfate. The mixture was purged with nitrogen for 15 minutes. The gas rate was then reduced and 12.5 g of vinyl acetate and 1.25 g of butyl acrylate were added to the flask. A mixture containing 31 g of glyoxalated butyl maleurate (Example 1), 2.5 g of 20% ethoxalated alkylphenol (GAF IGEPAL CA-620), 4.7 g of sodium dodecylbenzene sulfonate, 50 g of vinyl acetate and 36.2 g of butyl acrylate was stirred vigorously in a beaker, then transferred to the addition funnel. A catalyst solution of 0.18 g of ammonium persulfate and 7.5 g of distilled water was also prepared.

The mixture in the flask was heated to 72°–75° C. The polymerization started to take place and a latex was formed. After one hour, the mixture in the addition funnel and the catalyst solution were added slowly into the flask over four hours. The reaction mixture was heated at 75° C. for an additional hour before it was cooled to room temperature. The resulting latex weighed 23.5 g and contained 39% solids.

B. Self-crosslinking of Latex Polymer

Thin layer latex polymer films were drawn on aluminum plates. The films were air dried overnight or cured at 120° C. for 30 minutes. The cured films were insoluble and swollen by water, acetone, methylene chloride, DMF and DMSO. The films cured at 126° C. also showed good chemical resistance properties (MEK double rubs>90).

EXAMPLE 17C–26

A. All-Acrylic Latex

The following general procedure was used in the synthesis of all acrylic latexes containing the monomers of the present invention.

A 1 liter glass jacketed resin reactor with a bottom discharge valve is used. The reactor is equipped with thermometer, a circulating constant temperature heating bath, $N_2$ purge, a teflon turbin agitator, a monomer emulsion feed pump calibrated for 4.59 g/min and an initiator feed pump calibrated for 0.5 g/min.

The following charge is used:

| | Wt. (g) |
|---|---|
| Reactor Charge | |
| D.I. Water | 192.1 |
| Monomer Emulsion | |
| D.I. Water | 182.6 |
| Rhodacal ® DS4 (Surfactant)* | 21.7 |
| WAM Monomer | 5.0 |
| Methylmethacrylate | 260.0 |
| Butylacrylate | 30.0 |
| Methacrylic acid | 2.7 |
| Initiator Solution | |
| Ammonium Persulfate | 2.0 |
| D.I. Water | 98.0 |

*23% solution in water; product of Rhône-Poulenc Co.

The monomer emulsion is prepared as follows:
1. Dissolve the surfactant in water.
2. If the monomer is only water soluble, add it to the water surfactant solution.
3. Blend all the monomers together. If the monomer is soluble in the organic phase, dissolve it in the monomer.
4. Finally, mix the monomers with the water surfactant solution and keep the mixture agitated to insure a homogeneous dispersion.

B. Polymerization Procedure

1. Heat the reactor water to 80° C. while the system is under a $N_2$ blanket.
2. At 80° C. add 25 grams of initiator solution and 14.2 grams of monomer emulsion. Hold at ~80° C. for 15 minutes.
3. Feed the remainder of the monomer emulsion and initiator solutions over a 2.5 hour period using the appropriate calibrated pumps. Maintain a polymerization temperature of 80±1° C.
4. After completion of the monomer and initiator addition, heat to 85° C. for 30 minutes.
5. Cool the emulsion to 23°–25° C. and adjust the pH to 9.0±0.2 with 28% $NH_4OH$. Filter the emulsion through a cheesecloth paint filter.

The yield should be ~955 grams, a viscosity of 20–28 cps and solis of ~50%.

The physical properties of some of the latexes prepared according to the above-described procedure, using the monomers of the present invention, are summarized in Table I below. Included for comparision is the latex containing no crosslinking monomer (L-C).

TABLE I

| | | | | Physical Properties | |
|---|---|---|---|---|---|
| Example | Latex ID | Monomer | pH | % Solids | Particle Size |
| 17C | L-C | None | 9.02 | 49.3 | 0.21–0.25 |
| 18 | L-M1 | M1 | 9.07 | 50.6 | 0.21–0.25 |
| 19 | L-M6 | M6 | 9.03 | 50.0 | 0.21–0.25 |
| 20 | L-M11 | M11 | 9.02 | 50.3 | 0.21–0.25 |
| 21 | L-M5 | M5 | 9.01 | 50.2 | 0.21–0.25 |
| 22 | L-M7 | M7 | 9.06 | 50.1 | 0.21–0.25 |
| 23 | L-M12 | M12 | 9.07 | 50.4 | 0.21–0.25 |
| 24 | L-M13 | M13 | 9.02 | 51.3 | 0.21–0.25 |
| 25 | L-M14 | M14 | 9.06 | 49.8 | 0.21–0.25 |

*C = Comparative Example

The latexes derived from the monomers of the present invention were cast into thin films, air-dried and cured at 130° C. for 5 minutes in a forced-air oven. Air-dried films were found to be soluble in MEK and DMF except for the acrylated glycomaleurate and similar doubly unsaturated monomers which produced crosslinker insoluble films. Cured films were insoluble in all cases. The results are shown in Table II, below.

TABLE II

Self-Crosslinking of All-Acrylic Latexes Using Glyoxylated Monomers of the Invention

| | | Film Solubility | |
|---|---|---|---|
| Example No. | Glyoxylated Monomer # | Air-Dried | Cured at 130° C./5 min |
| 17C | None (Control) | Soluble | Soluble |
| 18 | M1 | Soluble | Insoluble |
| 19 | M6 | Soluble | Insoluble |
| 20 | M11 | Insoluble | Insoluble |
| 21 | M5 | Insoluble | Insoluble |
| 22 | M7 | Soluble | Insoluble |
| 23 | M12 | Insoluble | Insoluble |
| 24 | M13 | Soluble | Insoluble |
| 25 | M14 | Soluble | Insoluble |

Paper Sizing

The examples below illustrate the use of higher alkyl glycomaleurates and related compounds as sizing agents for paper. A 2% solution containing 0.14 g of glyoxalated alkyl maleurate and 49.86 g of toluene was prepared. The solution was used to impregnate sheets (Whatman Qualitative 1 filter paper) to dose 0.08% (based on weight of the paper) of the sizer. The sheets were dried in an oven at 150° C. for 3 minutes. Sizing evaluations were performed by means of a liquid penetration test. Water containing a green dye (green buffer, pH 6.8) was used as test liquid. For comparison purposes, the same evaluations were performed side by side on ACCOSIZE®-17, a commercial paper size and higher alkyl maleurates, the precursors to glycomaleurates. The results presented below show that the $C_{18}$-glycomaleurate performs equivalently to the commercial ACCOSIZE®-17 and that the non-glyoxylated precursor ($C_{18}$-maleurate) is ineffective.

| | Test Material | Penetration time (seconds) |
|---|---|---|
| Example 26 | Glyoxylated Octadecyl Maleurate ($C_{18}$-Glycomaleurate) | >2000 |
| Example 27C | ACCOSIZE ®-17 | >2000 |
| Example 28C | Octadecyl Maleurate ($C_{18}$-Maleurate) | <10 |

*C = Compartative Example

EXAMPLES 29–31

Following the test procedure of Example 27, substantially similar results were obtained with the $C_{18}$-glycoitaconurates of Example 9, $C_{18}$-glycoitaconurate of Example 10 and $C_{18}$-glycofumaurate of Example 15.

Although the present invention is described with reference to certain preferred embodiments, it is apparent that variations or modifications thereof may be made by those skilled in the art without departing from the scope of this invention as defined by the appended claims.

What is claimed is:

1. A composition comprising a compound of the formula (I)

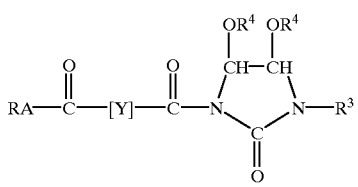

wherein A is —NH— or —O—;
wherein Y is

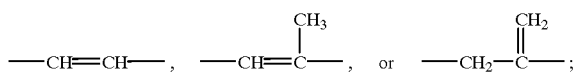

wherein R is H, an alkyl group having from 1 to 24 carbon atoms,

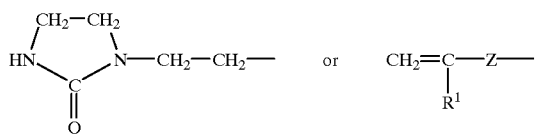

wherein Z is —$CH_2$—,

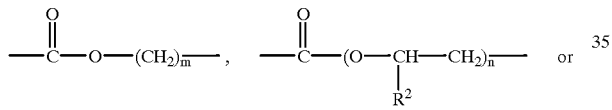

with the proviso that when A is —NH—, Z is $CH_2$—;
   wherein each $R^1$ or $R^2$ is, individually, hydrogen or $CH_3$, m is $\geq 2$ and n is an integer of from 1–5, inclusive; and
   wherein $R^3$ is hydrogen, an alkyl group having from 1 to 4 carbon atoms, a hydroxymethyl group or an alkoxymethyl group having from 2 to 6 carbon atoms, and each $R^4$ is, individually, hydrogen or an alkyl group having from 1 to 6 carbon atoms.

2. A latex composition comprising a latex polymer which is the reaction product of (a) monomers containing at least one ethylenically unsaturated group and (b) a compound represented by the formula (I)

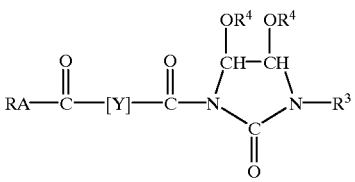

wherein A is —NH— or —O—;
wherein Y is

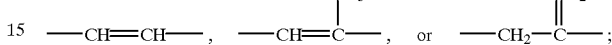

wherein R is H, an alkyl group having from 1 to 24 carbon atoms,

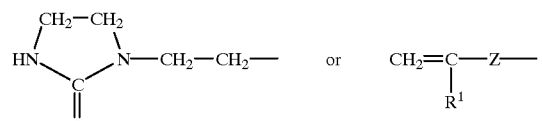

wherein Z is —$CH_2$—,

with the proviso that when A is —NH—, Z is $CH_2$—;
   wherein each $R^1$ or $R^2$ is, individually, hydrogen or $CH_3$, m is $\geq 2$ and n is an integer of from 1–5, inclusive; and
   wherein $R^3$ is hydrogen, an alkyl group having from 1 to 4 carbon atoms, a hydroxymethyl group or an alkoxymethyl group having from 2 to 6 carbon atoms, and each $R^4$ is, individually, hydrogen or an alkyl group having from 1 to 6 carbon atoms.

3. The latex composition of claim 2, wherein the ethylenically unsaturated monomer is selected from the group consisting of acrylic and methacrylic acids and their alkyl esters with alcohols having from 1 to 12 carbon atoms, vinyl esters of linear and branched carboxylic acids having from 1 to 25 carbon atoms, styrene, substituted styrene and α-methyl styrene and their substituent acids having from 1 to 4 carbon atoms and halogenated styrene having from 1 to 4 carbon atoms.

* * * * *